United States Patent [19]

Lafon

[11] Patent Number: 4,912,110
[45] Date of Patent: Mar. 27, 1990

[54] ANTIDEPRESSIVE SUBSTITUTED PHENYLPIPERAZINE COMPOUNDS

[75] Inventor: Louis Lafon, Paris, France

[73] Assignee: Laboratoire L. Lafton, Maisons Alfort, France

[21] Appl. No.: 283,736

[22] Filed: Dec. 13, 1988

Related U.S. Application Data

[63] Continuation-in-part of Ser. No. 891,298, Jul. 31, 1986, abandoned.

[30] Foreign Application Priority Data

Jul. 31, 1985 [FR] France ................. 85 11684

[51] Int. Cl.$^4$ .................. A61K 31/495; C07D 295/00
[52] U.S. Cl. ........................ 514/255; 544/403
[58] Field of Search .................. 514/255; 544/403

[56] References Cited

U.S. PATENT DOCUMENTS 4,166,180 8/1979 Kato et al. .................. 544/403

FOREIGN PATENT DOCUMENTS 3420782 10/1985 Fed. Rep. of Germany ...... 544/403
8447M 7/1971 France .
2351108 12/1977 France .

OTHER PUBLICATIONS

Hokusiku Pharmaceutical Co. Ltd., CA 101: 90977e (1984).
Parke, CA-55-8444i.

Primary Examiner—Cecilia Shen
Attorney, Agent, or Firm—Fleit, Jacobson, Cohn, Price, Holman & Stern

[57] ABSTRACT

The present invention relates, by way of new industrial products, to phenylpiperazine derivatives selected from the group comprising 3-methyl-2-phenylpiperazine, 1-isopropyl-3-phenylpiperazine, 1-ethyl-2-methyl-3-phenylpiperazine, 1-isopropyl-2-methyl-3-phenylpiperazine, 1,2,4-trimethyl-3-phenylpiperazine, and (halogenophenyl)alkyl-piperazines of the formula:

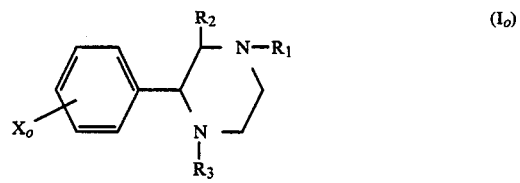

(wherein $X_o$ is F, Cl or Br, $R_1$ is H or $C_1$–$C_4$ alkyl, $R_2$ is H or $C_1$–$C_2$ alkyl and $R_3$ is H or $C_1$–$C_4$ alkyl, at least one of the symbols $R_1$, $R_2$ and $R_3$ being different from H), and addition salts thereof.

These new products are useful as antidepressants for the CNS.

10 Claims, No Drawings

ANTIDEPRESSIVE SUBSTITUTED PHENYLPIPERAZINE COMPOUNDS

CROSS REFERENCE

This invention is a continuation-in-part application of a previous U.S. patent application Ser. No. 891,298 filed on Jul. 31, 1986, now abandoned.

It comprises elements disclosed in said previous patent application and new comparison data with compounds according to the prior art teaching.

FIELD OF THE INVENTION

The present invention relates to new industrial products, namely phenylpiperazine derivatives of the formula I below and addition salts thereof. The invention also relates to the method for their preparation and their use in therapy, in particular as antidepressants for the central nervous system (CNS).

PRIOR ART

It is known that a number of phenylpiperazine derivatives have already been proposed in the past. In particular, compounds of the formula:

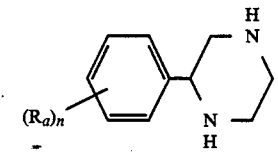

(Ia)

wherein $R_a$ represents a halogen atom or a $C_1$–$C_8$ alkyl, $C_1$–$C_8$ alkoxy, nitro, cyano or benzyloxy group, it being possible for two groupes R, taken-together, to form a methylenedioxy radical, and n is an integer having the value 1, 2 or 3, have been proposed in Patent Document FR-A-2 351 108 and corresponding U.S. Pat. No. US-A-4 166 180 as analgesics, vasodilators and antispasmodics.

It is known that compounds of the formula:

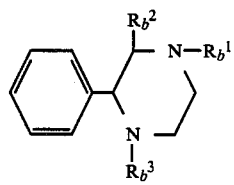

(Ib)

wherein $R_b{}^3$ represents (i) an alkyl group containing fewer than 5 carbon atoms, (ii) a phenyl group which can be substituted, or (iii) a phenylalkyl group which can be substituted on the phenyl nucleus and in which the alkyl radical contains fewer than 5 carbon atoms, $R_b{}^1$ is an alkyl group containing fewer than 5 carbon atoms or a phenylalkyl group in which the alkyl radical contains fewer than 3 carbon atoms, and $R_b{}^2$ represents the hydrogen atom or an alkyl group containing fewer than 5 carbon atoms, have also been proposed in FR-M-8477 as coronary dilators capable, if appropriate, of possessing sedative effects.

German patent document German Pat. No. 3 420 782 suggests to prepare 2-cyclohexylpiperazine compounds by hydrogenation of 2-phenylpiperazine products in which the piperazinyl ring comprises no substituent other than the phenyl ring, then to use said 2-cyclohexylpiperazine compounds as intermediates for obtaining antibacterials such as quinolin-4-one-3-carboxylic acid derivatives presenting on the 7 position a cyclohexylpiperazinyl substitution.

Japanese (Kokai) patent document JP-A-59 029 695 [as summed up in C.A. 101 90 277e (1984)] discloses similarly the use of 2-phenylpiperazine products (wherein the phenyl ring is a substituted phenyl group) as intermediates or starting materials for obtaining antibacterials such as quinolin-4-one-3-carboxylic acid derivatives presenting on the 7 position a phenylpiperazinyl substitution.

OBJECT OF THE INVENTION

It has now been found that compounds of the formula I below, which are not specifically described or seriously suggested by the prior art referred to above, are particularly valuable as antidepressants for the CNS.

The phenylpiperazine compounds according to the invention, which correspond to the general formula:

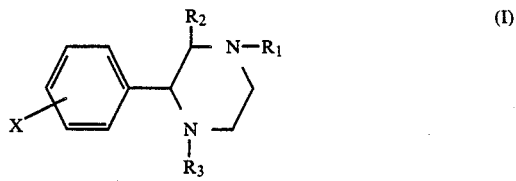

(I)

wherein:

$R_1$ represents the hydrogen atom or a $C_1$–$C_4$ alkyl group, $R_2$ represents the hydrogen atom or a $C_1$–$C_2$ alkyl group, $R_3$ represents the hydrogen atom or a $C_1$–$C_4$ alkyl group and X represents H, F, Cl or Br, at least one of the symbols $R_1$, $R_2$, $R_3$ and X being different from H, are selected from the group consisting of:

(1°) 3-methyl-2-phenylpiperazine,
(2°) 1-isopropyl-3-phenylpiperazine,
(3°) 1-ethyl-2-methyl-3-phenylpiperazine,
(4°) 1-isopropyl-2-methyl-3-phenylpiperazine,
(5°) 1,2,4-trimethyl-3-phenylpiperazine,
(6°) (halogenophenyl)alkylpiperazines which have, in their molecule, a halogen atom present on the phenyl ring and at least one alkyl group present on the piperazinyl ring, and which correspond to the general formula:

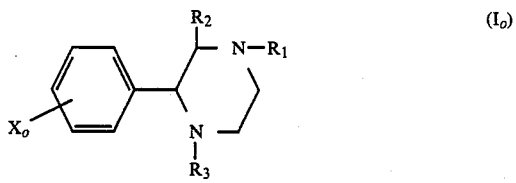

(I$_o$)

wherein $X_o$ is F, Cl or Br and $R_1$, $R_2$ and $R_3$ are defined as indicated above, with the additional proviso that at least one of the said symbols $R_1$, $R_2$ and $R_3$ is different from H, and (7°) addition salts thereof.

In accordance with the IUPAC nomenclature rules, the phenyl ring of the compounds of the formula I is shown as being located in the 2-position or 3-position of the piperazinyl ring according to the location of the other substituents of the said ring. It is for this reason that, in order to apply the systematic nomenclature to the compounds of the formula I and their synthesis intermediates, the 1-position of the piperazinyl ring:

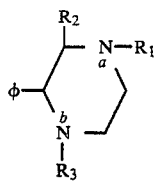

has hereafter been assigned to nitrogen atom "a" when $R_1$ is different from H or, conversely, to nitrogen atom "b" when $R_1$ is H.

Addition salts are understood here as meaning, on the one hand, the acid addition salts obtained by reacting a free base of the formula I with a mineral or organic acid, and, on the other hand, the ammonium salts. Among the acids which can be used to form salts with the free bases of the formula I, hydrochloric, hydrobromic, acetic, formic, propionic, oxalic, fumaric, maleic, succinic, benzoic, cinnamic, mandelic, citric, malic, tartaric, aspartic, glutamic, methanesulfonic and p-toluenesulfonic acids may be mentioned in particular. Among the compounds making it possible to obtain ammonium salts, alkyl halides (especially $C_1$-$C_{10}$), aryl halides and aralkyl halides may be mentioned in particular, especially the bromides, chlorides and iodides. In general, the acid addition salts are preferred to the ammonium salts.

A number of typical compounds according to the invention have been collated in Table I below without in any way implying a limitation.

(a) the compounds of the formula I wherein $R_1$ is H or $C_1$-$C_4$ alkyl, $R_2$ is $C_1$-$C_2$ alkyl, $R_3$ is H or $C_1$-$C_4$ alkyl and X is H; and (b) the compounds of the formula I wherein $R_1$ is $C_1$-$C_4$ alkyl, $R_2$ is H or $C_1$-$C_2$ alkyl, $R_3$ is H or $C_1$-$C_4$ alkyl and X is a halogen atom (preferably 2-Cl, 2-Br or 2-F).

Of these preferred compounds, the most valuable from the therapeutic point of view are those which present a phenyl ring substituted by a halogen atom (X=F, Cl or Br) and a piperazinyl ring substituted by a N-alkyl group, such as 3-methyl-2-phenylpiperazine, 1-ethyl-3-(2-chlorophenyl)-piperazine, 1-ethyl-3-(2-fluorophenyl)piperazine and addition salts thereof, especially the dihydrochlorides.

The compounds of the formula I can be prepared according to a method known per se by the application of conventional reaction mechanisms. The method of preparation recommended here consists in:

(A) reacting a 1-phenylalkane-1,2-dione of the formula:

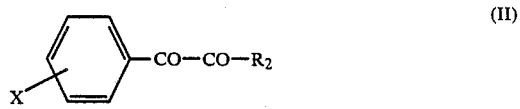

(II)

wherein X and $R_2$ are defined as above, with ethylenediamine $$H_2NCH_2CH_2NH_2 \quad \quad (III)$$

to give a 2-phenyldihydropyrazine of the formula:

(IV)

TABLE I

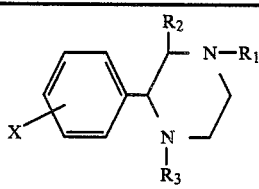

| Product | Code no. | X | $R_1$ | $R_2$ | $R_3$ | M.p. (c) |
|---|---|---|---|---|---|---|
| Ex. 1 (a) | CRL 41 223 | H | H | $CH_3$ | H | ≈ 260° C. (d) |
| Ex. 2 (a) | CRL 41 235 | H | $CH(CH_3)_2$ | H | H | 180–182° C. (e) |
| Ex. 3 (a) | CRL 41 270 | H | $CH_2CH_3$ | $CH_3$ | H | 198° C. |
| Ex. 4 (a) | CRL 41 271 | H | $CH(CH_3)_2$ | $CH_3$ | H | (f) |
| Ex. 5 (a) | CRL 41 272 | H | $CH_3$ | $CH_3$ | $CH_3$ | 190° C. |
| Ex. 6 (a) | CRL 41 202 | 4-Cl | $CH_3$ | H | H | 200° C. (d) |
| Ex. 7 (a) | CRL 41 228 | 3-Cl | $CH_2CH_3$ | H | H | 170° C. |
| Ex. 8 (a) | CRL 41 234 | 2-F | $CH_2CH_3$ | H | H | 210° C. (d) |
| Ex. 9 (a) | CRL 41 238 | 2-Cl | $CH_2CH_3$ | H | H | 215° C. (d) |
| Ex. 10 (a) | CRL 41 239 | 4-Cl | $CH_2CH_3$ | H | H | 208° C. (d) |
| Ex. 11 (a) | — | 2-Br | $CH_2CH_3$ | H | H | 221° C. |

Notes
(a): dihydrochloride
(b): free base
(c): instantaneous melting point
(d): with decomposition
(e): hygroscopic product
(f): oily product The group $R_1$ will advantageously represent a $C_1$-$C_4$ alkyl group; $R_1$ may also represent the hydrogen atom if the group $R_2$ is a $C_1$-$C_2$ alkyl group.

Among the compounds according to the invention which are preferred on account of their effects on the CNS, and in particular their antidepressant properties, the following may be mentioned in particular:

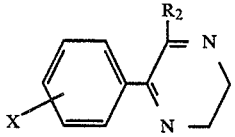

wherein X and $R_2$ are defined as above;

(B) subjecting the resulting compound of the formula IV to a reduction reaction with a reducing agent, selected especially from the group comprising LiAlH$_4$ and NaBH$_4$, to give a 2-phenylpiperazine of the formula I wherein R$_1$=R$_3$=H; and (C) if necessary, subjecting the resulting compound of the formula I wherein R$_1$=R$_3$=H to an alkylation reaction in order to introduce the group R$_1$=C$_1$-C$_4$ alkyl or the groups R$_1$ and R$_3$ each representing a C$_1$-C$_4$ alkyl group.

The cyclization reaction of stage A is advantageously carried out using an excess of ethylenediamine relative to the stoichiometric conditions (preferably with a molar ratio III:II of between 1.1 and 1.5), for at least 10 minutes, at a temperature of 15°-25° C. Lower alcohols, such as CH$_3$OH and C$_2$H$_5$OH, may be mentioned in particular as suitable solvents for the cyclization of stage A.

The reduction reaction of stage B is carried out with a borohydride or an aluminohydride, i.e. in this case LiAlH$_4$, NaBH$_4$ or a similar substance such as KBH$_4$. This reaction is carried out at a temperature of 0° to 25° C. for at least 10 minutes. In practice, the reduction reaction with aluminohydride is carried out at a low temperature (0° to 5° C.) for 10 to 30 minutes and the reduction reaction with borohydride is carried out at a low temperature (0° to 5° C.) for 15 to 60 minutes and then at room temperature (15°-20° C.) for at least 3 hours.

In stage C, the N-alkylation is carried out according to a conventional method to give either an N-monoalkylated derivative of the formula I (R$_1$=C$_1$-C$_4$ alkyl; R$_3$=H) or an N,N'-dialkylated derivative of the formula I (R$_1$=C$_1$-C$_4$ alkyl; R$_3$=C$_1$-C$_4$ alkyl).

The N-monoalkylation is advantageously carried out by reacting a compound of the formula I wherein R$_1$=R$_3$=H with a reagent selected from the group comprising:

(i) the alkyl halides of the formula:

R$_1$'Hal    (V)

wherein R$_1$' is a C$_1$-C$_4$ alkyl group and Hal is a halogen atom, in an alkaline medium (in the presence of Na+ or K+ ions), and (ii) the carboxylic acid esters of the formula:

R$_1$"—COO—Alk    (VI)

wherein Alk is a C$_1$-C$_3$ alkyl group (especially CH$_3$ and preferably C$_2$H$_5$) and R$_1$" is a C$_1$-C$_3$ alkyl group, in the presence of AlLiH$_4$, in an inert solvent such as tetrahydrofuran.

In the N-alkylation reaction with an alkyl halide R$_1$'Hal (wherein Hal is F, Cl, Br or I), it has been found that the iodides, such as ICH$_3$, favor alkylation of nitrogen atom "a".

In the N-alkylation reaction with an ester of the formula VI in the presence of the reducing agent AlLiH$_4$, it is the acyl radical R$_1$"CO which is involved. Thus, when R$_1$" is CH$_3$, the radical CH$_3$CO leads to the group R$_1$=C$_2$H$_5$, and when R$_1$" is C$_2$H$_5$, the radical CH$_3$CH$_2$CO leads to the branched group R$_1$=CH(CH$_3$)$_2$ in accordance with the reaction mechanism described by J. M. Khanna et al., Synthesis, Sept. 1975, pages 607-608.

The N-monoalkylation referred to above essentially concerns nitrogen atom "a". The N'-monoalkylation on nitrogen atom "b" can be carried out according to conventional procedures, for example (i) by using a catalyst which favors alkylation of nitrogen atom "b" in preference to nitrogen atom "a", or alternatively (ii) by reacting a 1-phenylalkane-1,2-dione of the formula II with an ethylenediamine of the formula:

H$_2$NCH$_2$CH$_2$NHR$_3$'    (III bis)

wherein R$_3$' is a C$_1$-C$_4$ alkyl group, and then isolating, from the reaction medium, the resulting cyclized derivative of the formula I (wherein R$_3$=C$_1$-C$_4$ alkyl and R$_1$=H) and its isomer (compound of the formula I wherein R$_3$=H and R$_1$=R$_3$').

The general method for carrying out the N,N'-dialkylation consists in subjecting an N-monoalkylated compound to an N'-alkylation reaction according to a known method. As a variant, the N,N'-dialkylation can be carried out directly by means of an alkyl formate of the formula VI (wherein R$_1$" is H), in the presence of AlLiH$_4$, to give a compound of the formula I wherein R$_1$=R$_3$=CH$_3$.

The compounds of the invention are all active on the CNS. They have in common the property of behaving as antidepressants in the organism. In their neuropsychopharmacological profile, in addition to their antidepressant properties, they also have stimulant and/or sedative effects according to the doses administered. Products of the formula I$_o$, such as CRL 41 238 (product of Example 11), additionally have beneficial immunomodulating effects.

A therapeutic composition recommended according to the invention contains, in association with a physiologically acceptable excipient, at least one phenylpiperazine derivative of this invention, or one of its non-toxic addition salts, as the active ingredient.

Of course, in a composition of this type, the active ingredient, which is selected from the group comprising the said derivatives of the formula I, non-toxic addition salts thereof and mixtures thereof, is present in a pharmaceutically effective amount.

To obtain an antidepressant drug for the CNS with a view to use in therapy for depressions and depressive states, it is recommended to use a substance belonging to the family of the phenylpiperazine derivatives of the formula I, as defined above, non-toxic addition salts thereof and mixtures thereof.

Also, to obtain an immunomodulating drug with a view to use in immunology, it is recommended to use 1-ethyl-3-(2-chlorophenyl)piperazine, its non-toxic addition salts, their analogs of the formula I$_o$ and mixtures thereof.

Further advantages and characteristics of the invention will be understood more clearly from the following description of preparative examples on the one hand and results of pharmacological tests on the other; these data as a whole do not in any way imply a limitation but are given by way of illustration.

PREPARATION I

Preparation of 3-methyl-2-phenylpiperazine dihydrochloride

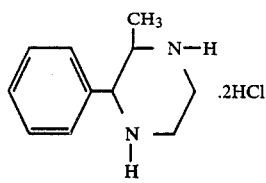

(Example 1; Code no.: CRL 41 223)

A solution of 5 g (0.0338 mol) of 1-phenylpropane-1,2-dione and 2.5 g (0.0417 mol) of ethylenediamine in 300 ml of methanol is left to stand for 0.5 hour. It is cooled with an ice bath, 5 g (0.132 mol) of $NaBH_4$ are added and the mixture is left to stand overnight. It is evaporated to dryness, the evaporation residue is taken up with water, extraction is carried out with chloroform, the chloroform solution is washed with water, dried over $MgSO_4$ and filtered to remove the $MgSO_4$, and the filtrate is then evaporated to dryness. The evaporation residue is taken up with methanol, the mixture is acidified with a solution of hydrochloric acid in ethanol ($C_2H_5OH$ containing 3N HCl) and evaporated to dryness, the evaporation residue is taken up with $CH_3COCH_3$ and the crystals formed are filtered off. Recrystallization from methanol gives 3 g (yield: 36%) of CRL 41 223.

M.p.$_{inst.}$ ≃ 260° C. (decomposition).

Analysis { measured % $Cl^-$: 27.99%
theoretical % $Cl^-$: 28.51% }

PREPARATION II

Preparation of 1-ethyl-2-methyl-3-phenylpiperazine dihydrochloride (Example 3; Code no.: CRL 41 270)

A solution of 0.169 mol of 3-methyl-2-phenylpiperazine in 250 ml of anhydrous tetrahydrofuran (THF) is run into a suspension of 25 g of $AlLiH_4$ in 1000 ml of anhydrous THF. The mixture is left to stand for 0.25 hour after the introduction has ended and 83 ml of $CH_3CO_2C_2H_5$ are then run in slowly. The mixture is left to stand for 0.25 hour after the introduction has ended and 3N NaOH is then cautiously run in. The mixture is filtered, the filtrate is evaporated to dryness, the evaporation residue is taken up with water, extraction is carried out with chloroform and the chloroform phase is washed with water and dried over $MgSO_4$. It is filtered (to remove the $MgSO_4$), the filtrate is evaporated to dryness, the evaporation residue is taken up with $CH_3OH$, the medium is acidified with a solution of hydrochloric acid in ethanol and the resulting mixture is placed in a refrigerator. It is filtered (to remove the 3-methyl-2-phenylpiperazine dihydrochloride formed from the unreacted free base) and the filtrate is evaporated to dryness; recrystallization of the evaporation residue from a diethyl ether/ethanol mixture (1:1 v/v) gives 12 g (yield: 25.6%) of CRL 41 270.

M.p.$_{inst.}$ = 198° C.

PREPARATION III

Preparation of 1-isopropyl-2-methyl-3-phenylpiperazine dihydrochloride (Example 4; Code no.: CRL 41 271)

42 g (0.169 mol) of 3-methyl-2-phenylpiperazine dihydrochloride (CRL 41 223, obtained by preparative method I) are dissolved in $H_2O$ and neutralized with NaOH, extraction is carried out with $CHCl_3$ and the chloroform phase is washed with water and dried over $MgSO_4$. It is filtered, the filtrate is evaporated to dryness and the evaporation residue is then taken up with anhydrous THF.

The resulting solution (which contains the free base of CRL 41 223) is run into a suspension of 25 g of $AlLiH_4$ in 1000 ml of THF. The mixture is left to stand for 0.25 hour after the introduction has ended. 98 ml of $CH_3CH_2CO_2C_2H_5$ are run in slowly and the mixture is left to stand for 0.25 hour after the introduction has ended. 3N NaOH is then cautiously run in, the mixture is filtered, the filtrate is evaporated to dryness, the evaporation residue is taken up with $CH_3OH$ and the mixture is acidified with a solution of hydrochloric acid in ethanol and placed in a refrigerator. The precipitate of CRL 41 223 (which has formed from the unreacted free base) is filtered off and the filtrate is evaporated to dryness. Recrystallization of the evaporation residue from a diethyl ether/ethanol mixture (1:1 v/v) gives 7.8 g (yield: 16%) of CRL 41 271 in the form of an oil.

PREPARATION IV

Preparation of 1-ethyl-3-(2-chlorophenyl)piperazine dihydrochloride (Example 9; Code no.: CRL 41 238)

18.86 g (0.070 mol) of 2-(2-chlorophenyl)piperazine dihydrochloride (m.p.$_{inst.}$=230° C.; product described in Patent Document FR-A-2 351 108; see page 6 line 1 of the said French document) are dissolved in $H_2O$ and neutralized with NaOH, extraction is carried out with $CHCl_3$, the chloroform solution is washed with water, dried with $MgSO_4$ and filtered, the filtrate is evaporated to dryness and the evaporation residue is taken up with 200 ml of anhydrous THF. This solution is run into a suspension of 10 g of $AlLiH_4$ in 1000 ml of anhydrous THF. The mixture is left to stand for 10 minutes and 20 ml of $CH_3CO_2C_2H_5$ are then run in slowly. The reaction medium is left to stand for 0.5 hour and 3N NaOH is added. The mixture is filtered, the filtrate is evaporated to dryness, the evaporation residue is taken up with $H_2O$, extraction is carried out with $CHCl_3$ and the chloroform solution is washed with $H_2O$ and dried over $MgSO_4$. It is filtered, the filtrate is evaporated to dryness, the evaporation residue is taken up with $CH_3OH$ and the mixture is acidified with a solution of hydrochloric acid in ethanol. After cooling in a refrigerator, the precipitate formed [which contains 2-(2-chlorophenyl)piperazine dihydrochloride] is filtered off and the filtrate is evaporated to dryness; recrystallization of the evaporation residue from an acetone/ethanol mixture (1:1 v/v) gives 7.2 g (yield: 34.6%) of CRL 41 238.
M.p.$_{inst.}$=215° C. (decomposition).

PREPARATION V

Preparation of 1-methyl-3-(4-chlorophenyl)piperazine dihydrochloride (Example 6; Code no.: CRL 41 202)

A mixture of 10 g (0.051 mol) of 2-(4-chlorophenyl)-piperazine (comparison product CP 1 of Table IV below; M.p=124° C.) 10.80 g (0.102 mol) of Na$_2$CO$_3$, 7.24 g (0.051 mol) of ICH$_3$ and 100 ml of water is heated under reflux for 6 hours. It is cooled, extraction is carried out with CHCl$_3$ and the chloroform phase is washed with water and dried over MgSO$_4$. It is filtered, the filtrate is evaporated to dryness, the evaporation residue is taken up with CH$_3$OH and the mixture is acidified with a solution of hydrochloric acid in ethanol. It is evaporated to dryness; recrystallization of the evaporation residue from a methanol/ethyl acetate mixture (1:1 v/v) gives 3 g (yield: 20.8%) of CRL 41 202. M.p.$_{inst.}$=200° C. (decomposition).

PREPARATION VI

Preparation of 1,2,4-trimethyl-3-phenylpiperazine dihydrochloride (Example 5; Code no.: CRL 41 272)

A solution of 0.169 mol of 3-methyl-2-phenylpiperazine in anhydrous THF is run into a suspension of 25 g of AlLiH$_4$ in 1000 ml of THF. The mixture is left to stand for 0.25 hour after the introduction has ended and 67 ml of ethyl formate are then run in slowly. The mixture is left to stand for 0.25 hour after the introduction has ended and 3N NaOH is then cautiously run in. The mixture is filtered, the filtrate is evaporated to dryness, the evaporation residue is taken up with H$_2$O, extraction is carried out with CHCl$_3$ and the chloroform solution is washed with H$_2$O and dried over MgSO$_4$. It is filtered, the filtrate is evaporated to dryness, the evaporation residue is taken up with CH$_3$OH and the mixture is acidified with a solution of hydrochloric acid in ethanol. The resulting mixture is placed in a refrigerator, the precipitate of CRL 41 223 (which has formed from the corresponding unreacted free base) is filtered off, the filtrate is evaporated to dryness and recrystallization of the evaporation residue from a diethyl ether/ethanol mixture (1:1 v/v) then gives 13 g (yield: 28%) of CRL 41 272. M.p.$_{inst.}$=190° C.

PREPARATION VII

Preparation of 1-isopropyl-3-phenylpiperazine hydrochloride (Example 2; Code no.: CRL 41 235)

By following the procedure indicated in preparation V above and replacing ICH$_3$ with ICH(CH$_3$)$_2$, CRL 41 235 is obtained with a yield of 25%. M.p.=180°–182° C. (hygroscopic product).

Tests which were undertaken with the compounds according to the invention have been summarized below.

A. TESTS RELATING TO CRL 41 238 (PRODUCT OF EXAMPLE 9)

In the neuropsychopharmacological study which follows, a solution of CRL 41 238 in distilled water was administered intraperitoneally in a volume of 20 ml/kg to male mice and 5 ml/kg to male rats.

The pH of the injected solution varies as a function of the concentration of CRL 41 238, as indicated in Table II below.

TABLE II

| pH of CRL 41 238 as a function of concentration | |
| --- | --- |
| Concentration | pH |
| 50 g/l | 2.0 |
| 26 g/l | 2.5 |
| 13 g/l | 3.0 |
| 6 g/l | 3.5 |
| 2 g/l | 4.0 |

TABLE II-continued

| pH of CRL 41 238 as a function of concentration | |
| --- | --- |
| Concentration | pH |
| 0.8 g/l | 4.5 |
| 0.4 g/l | 5.0 |
| ≦0.05 g/l | 5.5 |

I. TOXICITY

In male mice, the LD$_0$ (maximum non-lethal dose) by intraperitoneal administration is greater than 128 mg/kg and the LD$_{100}$ (minimum lethal dose for all the animals tested) is less than or equal to 256 mg/kg.

II. OVERALL BEHAVIOR AND REACTIVITIES

Groups of three animals are observed before and then 0.25 hour, 0.50 hour, 1 hour, 2 hours, 3 hours and 24 hours after the administration of CRL 41 238. The following observations are made:

(1°) in mice at doses of 1 and 4 mg/kg:
  no distinct modification of the behavior and reactivities compared with the control group receiving only water, and
  hypothermia at a dose of 4 mg/kg;
at a dose of 16 mg/kg:
  sedation for 0.5 hour to 1 hour,
  hypothermia, and
  piloerection for 1 hour; and
at a dose of 64 mg/kg:
  sedation for 3 hours,
  a decrease in the breathing rate for 1 hour,
  a decrease in the reactivity to touch for 0.25 hour, and
  hypothermia for 3 hours, the maximum effect (−3.2° C.) being reached 0.5 hour after administration; and (2°) in rats at doses of 0.5 mg/kg, 2 mg/kg and 8 mg/kg:
  types of behavior, reactivities and variations in pupil diameter and rectal temperature which are substantially comparable to those of the control group receiving only distilled water; and
at a dose of 32 mg/kg:
  sedation and a decrease in the breathing rate for 3 hours,
  a decrease in the reactivity to touch and the muscular tonus for 1 hour, and
  moderate mydriasis for 1 hour.

III. INTERACTION WITH APOMORPHINE (1°) In mice

Groups of 6 mice receive CRL 41 238 0.5 hour before the subcutaneous injection of 1 or 16 mg/kg of apomorphine. It is observed that, at the high dose used (64 mg/kg), CRL 41 238 opposes the hypothermia induced by 16 mg/kg of apomorphine, and that the righting behavior and the stereotypies induced by 1 mg/kg and 16 mg/kg of apomorphine are practically unmodified by CRL 41 238 at the doses used.

(2°) In rats

CRL 41 238 is administered to groups of 6 rats 0.5 hour before the subcutaneous injection of 0.5 mg/kg of apomorphine. It is observed that CRL 41 238 does not modify the stereotypies induced by apomorphine.

IV. INTERACTION WITH AMPHETAMINE

Amphetamine (2 mg/kg) is injected intraperitoneally into groups of 6 rats 30 minutes after the administration of CRL 41 238. It is found that, at the highest dose used (32 mg/kg), CRL 41 238 does not modify the stereotypies induced by amphetamine.

V. INTERACTION WITH RESERPINE

Four hours after the intraperitoneal injection of 2.5 mg/kg of reserpine, groups of 6 mice receive CRL 41 238.

It is noted that CRL 41 238 does not oppose the hypothermia and the ptosis induced by reserpine.

VI. INTERACTION WITH OXOTREMORINE

CRL 41 238 is administered to groups of 6 mice 0.5 hour before the intraperitoneal injection of 0.5 mg/kg of oxotremorine.

(1°) Action on the temperature

It is found that, at the highest dose used (64 mg/kg), CRL 41 238 opposes the hypothermic action of oxotremorine whereas, as from a dose of 4 mg/kg and especially at doses of 16 and 32 mg/kg, the said CRL 41 238 is hypothermic when administered by itself.

(2°) Action on the trembling

It is found that, at the highest dose used (64 mg/kg), CRL 41 238 decreases the intensity of the trembling induced by oxotremorine.

(3°) Action on the peripheral cholinergic symptoms

It is observed that CRL 41 238 does not modify the signs of peripheral cholinergic stimulation induced by oxotremorine.

VII. ACTION ON THE FOUR PLATE TEST, TRACTION AND ELECTRIC SHOCK

The test is performed on groups of 10 mice 30 minutes after the administration of CRL 41 238.

It is found that CRL 41 238 does not modify the number of punished passes, does not cause major motor incapacity and does not aggravate the convulsant and lethal effects of electric shock.

VIII. ACTION ON THE SPONTANEOUS MOTILITY 0.5 hour after they have received CRL 41 238, the mice (6 per dose, 12 control animals) are placed in an actimeter, where their motility is recorded for 30 minutes.

It is observed that, as from a dose of 1 mg/kg and especially at doses of 4 mg/kg and 64 mg/kg, CRL 41 238 decreases the spontaneous motor activity of the mice.

IX. ACTION ON THE INTERGROUP AGGRESSIVENESS

After they have stayed for 3 weeks in the two halves of a cage divided by an opaque partition, groups of 3 mice receive CRL 41 238. Half an hour later, the two groups from the same cage are brought together by removal of the partition and the number of fights which occur in 10 minutes is noted.

It is found that CRL 41 238 slightly decreases the number of fights. It should be pointed out that the results are not significant since the control animals were abnormally non-combative.

X. ACTION TOWARDS SOME FORMS OF BEHAVIOR PERTURBED BY VARIOUS AGENTS

(1°) Motility reduced by habituation to the enclosure

After they have stayed in the actimeters for 18 hours, the mice (6 per dose, 12 control animals) receive CRL 41 238. They are immediately returned to their respective enclosures and, half an hour later, their motility is recorded for 30 minutes.

It is observed that CRL 41 238 does not cause a distinct resumption in the motor activity of mice accustomed to their enclosure.

(2°) Motility reduced by hypoxic aggression

Half an hour after they have received CRL 41 238, the mice (10 per dose, 20 control animals) are subjected to acute hypobaric anoxia [pressure reduction of 600 mm Hg (i.e. about $8 \times 10^4$ Pa) in 90 seconds; release of vacuum in 45 seconds] and are then placed in an actimeter, where their motility is recorded for 10 minutes.

It is observed that CRL 41 238 does not cause a distinct improvement in the motor recovery of mice whose motility has been depressed following a brief period in a reduced-pressure enclosure.

(3°) Asphyxiant anoxia

Groups of 10 mice receive CRL 41 238 half an hour before the intraperitoneal administration of 32 mg/kg of gallamine triiodoethylate (reference curarizing agent).

It is observed that, for practical purposes, CRL 41 238 does not modify the time taken for convulsions and death to occur following asphyxiant anoxia caused by a curarizing agent.

XI. INTERACTION WITH BARBITAL

Half an hour after the administration of CRL 41 238, groups of 10 mice receive an intraperitoneal injection of barbital (220 mg/kg).

It is found that CRL 41 238 does not modify the duration of the sleep induced by barbital.

XII. ACTION ON THE "BEHAVIORAL DESPAIR"

Half an hour after they have received CRL 41 238, groups of 6 mice are placed in a beaker filled with water to a height of 6 cm. The total period of immobility between the 2nd and 6th minutes following immersion is noted.

It is observed that, as from a dose of 4 mg/kg and especially at doses of 8 mg/kg, 16 mg/kg, 32 mg/kg and 64 mg/kg, CRL 41 238 reduces the period of immobility of mice which have been forcibly immersed.

XIII. CONCLUSIONS

The above neuropsychopharmacological tests as a whole show that CRL 41 238 has:

antidepressant effects: moderate antagonism of the hypothermia induced by apomorphine, reserpine or oxotremorine at high doses in mice, and a distinct reduction in the period of immobility due to "despair" as from the lowest doses; and sedative effects: sedation in mice and rats with a decrease in the reactivities, hypothermia in mice and a decrease in the spontaneous motor activity of mice.

XIV. COMPLEMENT (IMMUNOLOGICAL STUDY)

CRL 41 238, at a dose of 100 mg/kg per os, is active on the cellular and humoral immunity according to the so-called test for cells forming lysis areas, described by A. J. CUNNINGHAM et al. ("Further improvements in the plaque technique for detecting single antibody forming cells"), Immunology 14, pages 599–601 (1968), and according to measurement of the intensity of the delayed hypersensitivity to the red blood corpuscles of sheep, described by T. E. MILLER et al. ("Immunopotentiation with BCG II modulation of the response to sheep blood cells"), Journal of the National Cancer Institute 51 (No. 5), pages 1669–1676 (1973). The corresponding tests show that CRL 41 238 behaves as an immunomodulating agent.

In clinical trails, CRL 41 238 proved to be a good antidepressant, in particular in the treatment of patients suffering from (i) psychotic depressions of the melancholic type, and (ii) depressive states of the neurotic type. The recommended daily dosage for adults is 45 to 90 mg of CRL 41 238 per os, in particular at a rate of 3 to 6 gelatine capsules per day, each containing 15 mg of active principle.

B. TESTS RELATING TO CRL 41 223 (PRODUCT OF EXAMPLE 1)

The neuropsychopharmacological study of CRL 41 223 was carried out as indicated above for CRL 41 238, except that the intraperitoneal administration to male mice (in a volume of 20 ml/kg) and male rats (in a volume of 5 ml/kg) took place after the CRL 41 223 had been suspended in an aqueous solution of gum arabic in the case of concentrations greater than 25 g/l, or dissolved in distilled water in the case of concentrations less than or equal to 25 g/l (pH 4.5).

(a) TOXICITY

In male mice, the $LD_0$ of CRL 41 223 by intraperitoneal administration is greater than 256 mg/kg and the $LD_{100}$ is less than or equal to 512 mg/kg.

(b) OVERALL BEHAVIOR AND REACTIVITIES (1°) In mice

Administered intraperitoneally to mice, CRL 41 223 causes the following effects at the following doses:
2 mg/kg:
 moderate mydriasis for 3 hours;
8 mg/kg:
 hypothermia which is at a maximum (−1.4° C.) 1 hour after administration, and
 moderate mydriasis for 3 hours;
32 mg/kg:
 sedation starting 0.25 hour after administration,
 hypothermia which is at a maximum (−3.3° C.) 0.5 hour after administration,
 moderate mydriasis for 3 hours,
 piloerection, and
 dyspnea; and
128 mg/kg:
 transitory sedation (for 0.25 hour) in 2/3 of the animals and then excitation 1 hour after administration, with an increase in the fear reaction and the reactivity to touch (for 1 hour),
 dyspnea,
 piloerection,
 hypothermia which is at a maximum (−2.3° C.) 0.50 hour after administration, and
 mydriasis for 3 hours.

(2°) In rats

By intraperitoneal administration to male rats, CRL 41 223 causes the following effects at the following doses:
1 mg/kg:
 moderate mydriasis for 3 hours;
4 mg/kg:
 sedation for 2 hours,
 piloerection, and
 substantial mydriasis for 3 hours;
16 mg/kg:
 sedation for 2 hours, with a decrease in the muscular tonus and the reactivity to touch,
 piloerection, and
 substantial mydriasis for 3 hours; and
64 mg/kg:
 transitory sedation 0.25 hour after administration, followed by excitation for 3 hours, with an increase in the reactivity to touch and noise,
 dyspnea,
 piloerection for 0.5 hour, and
 moderate mydriasis for 3 hours.

(c) NEUROPSYCHOPHARMACOLOGICAL PROFILE

As a whole, the other tests undertaken according to the procedures given above for CRL 41 238 show that CRL 41 223 has the following in its neuropsychopharmacological profile:
antidepressant effects demonstrated by antagonism of the hypothermia induced by apomorphine, reserpine and oxotremorine, on the one hand, and a decrease in the duration of the immobility due to "despair", on the other;
dose-dependent diphasic effects:
at low doses, sedative effects:
 a decrease in the spontaneous motor activity of mice, and
 hypothermia; and
at high doses, excitant effects:
 antagonism of the sleep induced by barbital,
 a moderate increase in the reactivity to touch,
 potentiation of the sterotypies induced by apomorphine and amphetamine, and
 a moderate increase in the spontaneous motor activity of mice and in the motor recovery of mice whose activity has been depressed following a brief period in a reduced-pressure enclosure; and finally
effects reflecting peripheral alpha-adrenergic stimulation, demonstrated by antagonism of the ptosis induced by reserpine, mydriasis, piloerection and apparently antagonism of the trembling caused by oxotremorine.

(d) COMPLEMENTARY TESTS

CRL 41 223 was studied for its cardiovascular effects by intraduodenal administration in solution in physiological serum (maximum concentration used: 56 g/l; pH 4).

(1°) A dog (weight: 13.9 kg), anesthetized with nembutal, receives CRL 41 223 by intraduodenal administration at successive doses of 0.1, 0.5, 1, 2.5, 5, 10 and 20 mg/kg. The blood pressure, the heart rate, the blood flow through the femoral artery, the blood flow through the vertebral artery, the rectal temperature and the skin temperature are measured.

It is found that CRL 41 223 is slightly hypertensive as from a dose of 2.5 mg/kg by increasing the systolic blood pressure, does not modify the heart rate, decreases the blood flow through the femoral artery, increases the blood flow through the vertebral artery as from a dose of 20 mg/kg and causes a moderate increase in the rectal temperature and skin temperature.

(2°) The effects of isoprenaline, tested on the same dog after a cumulative dose of 39.1 mg/kg, administered intraduodenally, are not modified. With 10 μg/kg of isoprenaline, the diastolic blood pressure changes from 132 mm Hg (i.e. about $1.75 \times 10^4$ Pa) to 24 mm Hg (i.e. about $3.2 \times 10^3$ Pa) after CRL 41 223, instead of changing from 136 mm Hg (i.e. about $1.81 \times 10^4$ Pa) to 24 mm Hg (i.e. about $3.2 \times 10^3$ Pa) in the control animals, and the heart rate changes from 190 beats/minute to 260 beats/minute instead of from 160 beats/minute to 270 beats/minute in the control animals.

(3°) The hypertension induced by norepinephrine in the same dog is greatly increased by CRL 41 223. With 2 μg/kg of norepinephrine, the systolic blood pressure changes from 160 mm Hg (i.e., about $2.13 \times 10^4$ Pa) to 344 mm Hg (i.e. about $4.58 \times 10^4$ Pa) after CRL 41 223, instead of from 152 mm Hg (i.e. about $2.02 \times 10^4$ Pa) to 280 mm Hg (i.e. about $3.73 \times 10^4$ Pa) in the control animals.

(e) CLINICAL STUDIES

In clinical trials on adult humans, CRL 41 223 was shown to be a good antidepressant for the CNS and of particular value in cases of insomnia at a daily dose of 150 to 250 mg, administered orally. The recommended dosage by oral administration is 2 gelatine capsules per day, each containing 100 mg of CRL 41 223.

C. TESTS RELATING TO OTHER PRODUCTS

The neuropsychopharmacological tests carried out with the other products according to the invention show especially that CRL 41 235 (Example 2), CRL 41 270 (Example 3), CRL 41 271 (Example 4), CRL 41 272 (Example 5), CRL 41 202 (Example 6), CRL 41 228 (Example 7), CRL 41 234 (Example 8) and CRL 41 239 (Example 10) all have antidepressant effects (demonstrated by antagonism of the hypothermia caused by apomorphine, reserpine and oxotremorine, on the one hand, and a decrease in the duration of immobility due to despair, on the other) and sedative effects (demonstrated by the hypothermia induced in mice, on the one hand, and a decrease in the spontaneous motor activity of mice, on the other).

However, a few particular mechanisms of action in the organism should be noted for the following products:

CRL 41 270 (Example 3) and CRL 41 239 (Example 10) paradoxically cause a decrease in the duration of the sleep induced by barbital in mice at high doses;

CRL 41 235 (Example 2), CRL 41 202 (Example 6), CRL 41 228 (Example 7) and CRL 41 239 (Example 10) exert effects reflecting peripher stimulation;

CRL 41 234 (Example 8), administered orally and gastrically, has antidepressant effects which mainly appear 0.5 hour after administration, and sedative effects which are particularly beneficial.

For information, the numerical results of tests relating to the products of Examples 2-8 and 10 according to the invention, in terms of the toxicity and the sedative effects (in this specific case the hypothermia induced by the said products in male mice by intraperitoneal administration, have been collated in Table III below.

COMPARATIVE ASSAYS

The compounds of the invention were teratogenically compared with products according to the prior art teaching listed in Table IV below which were prepared either according to said prior art teaching or according to the method of this invention.

The teratogenic study was carried out on female White New Zealand rabbits weighting each 2900-3000 grams before gestation which were administered with 5, 10, 50, 100 or 150 mg/kg of each product to be tested by gastrogavage from day 5 to day 18 of gestation, day 1 of gestation being the day on which a male rabbit is placed in the female's cage. A cesarean operation was then carried out on day 28 of the gestation, in order to enumerate:

(i) the total number of foetuses, and
(ii) the total number of foetuses presenting at least one malformation.

To appreciate the results of such a protocol it must be noted that natural malformations may occur. Statistically, the percentage of foetuses presenting at least one malformation in any control batch of gravid White New Zealand female rabbits is lower than or equal to 1.5% with respect to the total number of foetuses. The results which were obtained according to said protocol are given in Table V hereinafter.

Said results clearly show that, unlike the prior art products, the compounds according to this invention, in particular the compounds of examples 6-11, do not exhibit any harmful teratogenic effects.

TABLE III

| Product | Code no. | TOXICITY male mice i.p. (mg/kg) | HYPOTHERMIA male mice i.p. | | |
|---|---|---|---|---|---|
| | | | Dose (mg/kg) | Duration (hours) | Maximum value |
| Ex. 2 | CRL 41 235 | $LD_0 > 128$ | 4 | 1 | −1.2° C. at T + 0.5 h |
| | | $LD_{60} \simeq 250$ | 16 | 3 | −1.1° C. at T + 0.75h |
| | | $LD_{100} < 512$ | 64 | 3 | −2.6° C. at T + 1 h |
| Ex. 3 | CRL 41 270 | $LD_0 > 128$ | 64 | 3 | −2.5° C. at T + 0.5 h |
| | | $LD_{100} \leqq 256$ | | | |
| Ex. 4 | CRL 41 271 | $LD_{30} \simeq 60$ | 16 | 1 | −0.8° C. at T + 0.5 h |
| | | $LD_{60} \simeq 125$ | | | |
| | | $LD_9 > 128$ | 16 | 0.5 h | −1.3° C. at T + 0.3 h |
| Ex. 5 | CRL 41 272 | $LD_{30} \simeq 250$ | 64 | 3 h | −3.4° C. at T + 0.5 h |
| | | $LD_{100} \leqq 512$ | | | |
| Ex. 6 | CRL 41 202 | $LD_0 > 64$ | 32 | 3 h | −1.2° C. at T ± 2 h |

TABLE III-continued

| | | TOXICITY male mice i.p. | HYPOTHERMIA male mice i.p. | | |
|---|---|---|---|---|---|
| Product | Code no. | male mice i.p. (mg/kg) | Dose (mg/kg) | Duration (hours) | Maximum value |
| Ex. 7 | CRL 41 228 | $LD_{100} \leq 256$ $LD_0 > 64$ | 32 | 3 | −1.2° C. at T + 2 h |
| Ex. 10 | CRL 41 239 | $LD_{100} \leq 256$ $LD_0 > 128$ $LD_{60} \simeq 250$ | 16 64 | 2 3 | −0.9° C. at T + 1 h −3.0° C. at T + 0.5 h |
| Ex. 8 | CRL 41 234 | $LD_0 > 128$ $LD_{60} \simeq 250$ | 16 64 | 2 2 | −3.1° C. at T + 1 h −3° C. at T + 1 h |

TABLE IV

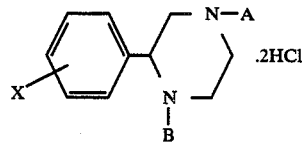

.2HCl

| Product | Code No | X | A | B |
|---|---|---|---|---|
| CP 1 (a, d) | — | — | 4-Cl | H | H |
| CP 2 (b) | — | H | Me | H |
| CP 3 | CRL 41 203 | 3-Cl | H | H |
| CP 4 (b) | — | H | Et | H |
| CP 5 (c) | — | H | Me | Me |
| CP 6 (d) | CRL 41 211 | 2-F | H | H |
| CP 7 (d) | — | 4-F | H | H |
| CP 8 (c) | — | H | Me | n-But |

TABLE IV-continued

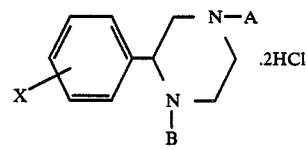

.2HCl

| Product | Code No | X | A | B |
|---|---|---|---|---|
| CP 9 (d) | — | 2-Cl | H | H |
| CP 10 (e) | — | 4-CH$_3$ | H | H |

Notes
(a): free base;
(b): prepared according to this invention in view of FR-M-8 447;
(c): according to FR-M-8 447;
(d): according to US-A-4 166 180;
(e): used as intermediate or starting material in DE-A-3 420 787 and in JP-A-59 029 685;

TABLE V

| Product | Code No | Dose mg/kg | Total gravid females (a) | Total foetuses (b) | Affected foetuses (C) number | % |
|---|---|---|---|---|---|---|
| Control batch | — | 0 | 19 | 182 | 2 (d) | 1.09 |
| Ex 6 | CRL 41 202 | 50 | 9 | 86 | 1 (e) | 1.16 (f) |
| Ex 6 | CRL 41 202 | 150 | 10 | 93 | 0 | 0 |
| Ex 7 | CRL 41 228 | 150 | 9 | 85 | 1 (g) | 1.17 (f) |
| Ex 8 | CRL 41 234 | 150 | 11 | 92 | 0 | 0 |
| Ex 9 | CRL 41 238 | 50 | 11 | 94 | 0 | 0 |
| Ex 9 | CRL 41 238 | 100 | 8 | 80 | 1 (e) | 1.25 (f) |
| Ex 9 | CRL 41 238 | 150 | 9 | 89 | 1 (e) | 1.12 (f) |
| Ex 10 | CRL 41 239 | 50 | 9 | 87 | 1 (h) | 1.14 (f) |
| Ex 10 | CRL 41 239 | 100 | 8 | 78 | 1 (i) | 1.28 (f) |
| Ex 10 | CRL 41 239 | 150 | 9 | 81 | 1 (e) | 1.23 (f) |
| Ex 11 | — | 150 | 9 | 87 | 1 (e) | 1.14 (f) |
| CP 1 | — | 100 | 8 | 78 | 1 (e) | 1.28 (f) |
| CP 1 | — | 150 | 8 | 79 | 4 (j) | 5.06 (k) |
| CP 2 | — | 100 | 8 | 73 | 5 (l) | 6.84 (k) |
| CP 3 | CRL 41 203 | 50 | 9 | 86 | 1 (m) | 1.16 (f) |
| CP 3 | CRL 41 203 | 100 | 10 | 94 | 0 | 0 |
| CP 3 | CRL 41 203 | 150 | 8 | . 78 | 6 (n) | 7.69 (k) |
| CP 4 | — | 100 | 8 | 78 | 4 (o) | 5.12 (k) |
| CP 5 | — | 150 | 9 | 80 | 6 (p) | 7.50 (k) |
| CP 6 | CR1 41 211 | 100 | 8 | 75 | 2 (q) | 2.66 (k) |
| CP 6 | CRL 41 211 | 150 | 7 | 44 (r) | 12 (s) | 27.27 |
| CP 7 | — | 100 | 8 | 77 | 3 (t) | 3.89 (k) |
| CP 8 | — | 100 | 7 | 49 (r) | 14 (u) | 28.57 |
| CP 9 | — | 150 | 9 | 76 | 5 (v) | 6.57 (k) |
| CP 10 | — | 100 | 8 | 72 | 4 (w) | 5.55 (k) |

TABLE V-continued

| Product | Code No | Dose mg/kg | Total gravid females (a) | Total foetuses (b) | Affected foetuses (C) number | % |
|---|---|---|---|---|---|---|
| CP 10 | — | 150 | 7 | 46 (r) | 17 (x) | 36.95 |

Notes
(a): Total number of gravid female rabbits.
(b): Total number of live foetuses.
(c): Live foetuses presenting malformation; the percentage is given with respect to the total number of live foetuses.
(d): Articular limb blocade: 1 case.
Anorous foetus: 1 case.
(e): Articular limb blocade: 1 case.
(f): Lower than the statistically upper "normal" limit of 1.5%.
(g): Deviated tail: 1 case.
(h): Shorter tail: 1 case.
(i): Anorous foetus: 1 case.
(j): Articular limb blocade: 2 cases.
Shorter or deviated tail: 2 cases.
(k): Higher than the statistically upper "normal" limit of 1.5%.
(l): Articular limb blocade: 2 cases.
Anorous foetus: 1 case.
Skull deformation: 2 cases.
(m): Deviated tail: 1 case.
(n): Exencephalia: 2 cases.
Shorter or deviated tail: 2 cases.
Anorous foetus: 1 case.
Articular limb blocade: 1 case.
(o): Articular limb blocade: 3 cases.
Anorous foetus: 1 case.
(p): Articular limb blocade: 3 cases.
Shorter or deviated tail: 2 cases.
Skull deformation: 1 case.
(q): Articular limb blocade: 2 cases.
(r): Lower than the average 8-10 live foetuses per litter as observed from the other results of Table V.
(s): Exencephalia: 2 cases.
Articular limb blocade: 6 cases.
Shorter or deviated tail: 4 cases.
(t): Execphalia: 1 case.
Articular limb blocade: 1 case.
Anorous foetus: 1 case.
(u): Execephalia: 2 cases.
Articular limb blocade: 4 cases.
Shorter or deviated tail: 6 cases.
Anorous foetus: 2 cases.
(v): Articular limb blocade: 2 cases.
Shorter or deviated tail: 2 cases.
Anorous foetus: 1 case.
(w): Articular limb blocade: 3 cases.
Deviated tail: 1 case..
(x): Skull deformation: 2 cases.
Articular limb blocade: 7 cases.
Shorter or deviated tail: 6 cases.
Anorous foetus: 2 cases.

What is claimed is:

1. A compound belonging to the family of substituted phenylpiperazines of the formula:

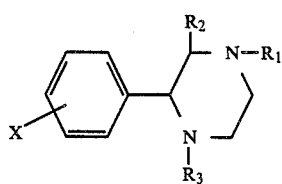

wherein:
$R_1$ is H or a $C_1$-$C_4$ alkyl group,
$R_2$ is H or a $C_1$-$C_2$ alkyl group,
$R_3$ is H or a $C_1$-$C_4$ alkyl group and
X is H, F, Cl or Br,
at least one of the symbols $R_1$, $R_2$, $R_3$ and X being different from H,
the said compound being selected from the group consisting of:
(1°) 3-methyl-2-phenylpiperazine,
(2°) 1-isopropyl-3-phenylpiperazine,
(3°) 1-ethyl-2-methyl-3-phenylpiperazine,
(4°) 1-isopropyl-2-methyl-3-phenylpiperazine,
(5°) 1,2,4-trimethyl-3-phenylpiperazine, (6°) (halogenophenyl)alkylpiperazines of the formula:

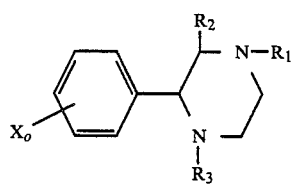

wherein $X_o$ is F, Cl or Br and $R_1$, $R_2$ and $R_3$ are as defined above, at least one of the symbols $R_1$, $R_2$ and $R_3$ being different from H, and
(7°) a pharmaceutically acceptable salt thereof.

2. A compound according to claim 1 which is selected from the group consisting of (i) the (halogenophenyl) alkyl-piperazine products of the formula

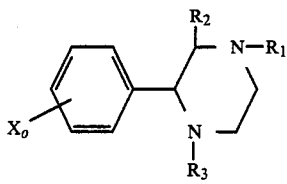

(I$_o$)

wherein X$_o$ is F, Cl or Br and R$_1$, R$_2$ and R$_3$ are as defined above, at least one of the symbols R$_1$, R$_2$ and R$_3$ being different from H, and (ii) a pharmaceutically acceptable salts thereof.

3. A compound according to claim 2, which is selected from the group consisting of (i) the (halogenophenyl)alkylpiperazine products of the formula I$_o$ wherein X$_o$ is F, Cl or Br, R$_2$ is H, R$_3$ is H, and R$_1$ is a C$_1$–C$_4$ alkyl group, and (ii) a pharmaceutically salts thereof.

4. A compound according to claim 3, wherein X$_o$ is 2-F, 2-Cl or 2-Br.

5. A compound according to claim 3 which is 1-ethyl-3-(2-fluorophenyl)piperazine, and a pharmaceutically acceptable salts thereof.

6. A compound according to claim 1 which is 3-methyl-2-phenylpiperazine, and a pharmaceutically salts thereof.

7. A compound according to claim 3, which is 1-ethyl-3-(2-chlorophenyl)piperazine, and a pharmaceutically salts thereof.

8. A compound according to claim 1, which is 1,2,4-trimethyl-3-phenylpiperazine, and a pharmaceutically salts thereof.

9. A compound according to claim 3, which is 1-ethyl-3-(2-bromophenyl)-piperazine and a pharmaceutically salts thereof.

10. A method for the treatment of depression and depressive states, comprising administering to a patient in need of such a treatment an antidepressive effective amount of a compound according to claim 1 or one of its non-toxic addition salts.

* * * * *